United States Patent
Moon et al.

(10) Patent No.: US 12,227,762 B2
(45) Date of Patent: Feb. 18, 2025

(54) SPHEROID CULTURE METHOD FOR NEURAL STEM CELL

(71) Applicant: Daegu Gyeongbuk Institute of Science and Technology, Daegu (KR)

(72) Inventors: Cheil Moon, Daegu (KR); Won Bae Jeon, Daegu (KR); Sam Hwan Kim, Daegu (KR); Seong Kyoon Choi, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 661 days.

(21) Appl. No.: 17/437,411

(22) PCT Filed: Mar. 11, 2020

(86) PCT No.: PCT/KR2020/003380
§ 371 (c)(1),
(2) Date: Sep. 8, 2021

(87) PCT Pub. No.: WO2020/184975
PCT Pub. Date: Sep. 17, 2020

(65) Prior Publication Data
US 2023/0174931 A1 Jun. 8, 2023

(30) Foreign Application Priority Data
Mar. 11, 2019 (KR) .................. 10-2019-0027632

(51) Int. Cl.
*C12N 5/0793* (2010.01)

(52) U.S. Cl.
CPC .......... *C12N 5/062* (2013.01); *C12N 2533/50* (2013.01)

(58) Field of Classification Search
None
See application file for complete search history.

(56) References Cited

FOREIGN PATENT DOCUMENTS

| JP | 2007-297401 | 11/2007 |
| KR | 1020130047404 | 5/2013 |
| KR | 1020140030396 | 3/2014 |
| KR | 1020140141182 | 12/2014 |
| KR | 1020150015919 | 2/2015 |
| KR | 1020160060794 | 5/2016 |
| KR | 1020180114860 | 10/2018 |

OTHER PUBLICATIONS

Jung GS, Lee KM, Park JK, Choi SK, Jeon WB. Morphogenetic and neuronal characterization of human neuroblastoma multicellular spheroids cultured under undifferentiated and all-trans-retinoic acid-differentiated conditions. BMB Rep. May 2013;46(5):276-81. (Year: 2013).*
Peng, H., Chen, Q., Zheng, J. (2014). Isolation and Culture of Neural Stem/Progenitor Cells. In: Xiong, H., Gendelman, H.E. (eds) Current Laboratory Methods in Neuroscience Research. Springer Protocols Handbooks. Springer, New York, NY. https://doi.org/10.1007/978-1-4614-8794-4_8 (Year: 2014).*
Nicolas C. Rivron et al., "Tissue deformation spatially modulates VEGF signaling and angiogenesis", PNAS, vol. 109, No. 18, 6886-6891, May 1, 2012.
Gabriele V. Ronnett et al., "Primary Culture of Neonatal Rat Olfactory Neurons", The Journal of Neuroscience, May 1991, 11(5): 1243-1255.
Won Bae Jeon et al., "Stimulation of fibroblasts and neuroblasts on a biomimetic extracellular matrix consisting of tandem repeats of the elastic VGVPG domain and RGD motif", J Biomed Mater Res A., May 2011;97(2):152-7. doi: 10.1002/jbm.a.33041. Epub Mar. 2, 2011.
Samhwan Kim et al., "Spheroid Culture of Mammalian Olfactory Receptor Neurons: Potential Applications for a Bioelectronic Nose", Exp Neurobiol 2018; 27(6): 574-592, Dec. 28, 2018.

* cited by examiner

*Primary Examiner* — Allison M Fox
*Assistant Examiner* — Qinhua Gu
(74) *Attorney, Agent, or Firm* — LEX IP MEISTER, PLLC

(57) ABSTRACT

The present invention relates to a method for culturing neural stem cells into spheroids, the method including: culturing neural stem cells in a culture vessel coated with a protein containing a VGVPG pentapeptide and an RGD integrin receptor ligand; and isolating the neural stem cells that are aggregated and formed into spheroids during the culturing.

10 Claims, 14 Drawing Sheets
Specification includes a Sequence Listing.

```
                        SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Primer of cyclophilin A (forward)

<400> SEQUENCE: 1
agcactgggg agaaaggatt                                                     20

<210> SEQ ID NO 2
<211> LENGTH: 20
<212> TYPE: DNA
<213> ORGANISM: Artificial Sequence
<220> FEATURE:
<223> OTHER INFORMATION: Primer of cyclophilin A (reverse)

<400> SEQUENCE: 2
agccactcag tcttggcagt                                                     20

<210> SEQ ID NO 3
<211> LENGTH: 20
<212> TYPE: DNA
<213> ORGANISM: Artificial Sequence
<220> FEATURE:
<223> OTHER INFORMATION: Primer of MAP2 (forward)

<400> SEQUENCE: 3
tgttgctgcc aagaaagatg                                                     20

<210> SEQ ID NO 4
```

```
<211> LENGTH: 20
<212> TYPE: DNA
<213> ORGANISM: Artificial Sequence
<220> FEATURE:
<223> OTHER INFORMATION: Primer of MAP2 (reverse)

<400> SEQUENCE: 4
acgtggctgg actcaatacc                                              20

<210> SEQ ID NO 5
<211> LENGTH: 20
<212> TYPE: DNA
<213> ORGANISM: Artificial Sequence
<220> FEATURE:
<223> OTHER INFORMATION: Primer of NSE (forward)

<400> SEQUENCE: 5
gtggaccaca tcaacagcac                                              20

<210> SEQ ID NO 6
<211> LENGTH: 20
<212> TYPE: DNA
<213> ORGANISM: Artificial Sequence
<220> FEATURE:
<223> OTHER INFORMATION: Primer of NSE (reverse)

<400> SEQUENCE: 6
tgagcaatgt ggcgatagag                                              20

<210> SEQ ID NO 7
<211> LENGTH: 20
<212> TYPE: DNA
<213> ORGANISM: Artificial Sequence
<220> FEATURE:
<223> OTHER INFORMATION: Primer of NST (forward)

<400> SEQUENCE: 7
tgaggcctcc tctcacaagt                                              20

<210> SEQ ID NO 8
<211> LENGTH: 20
<212> TYPE: DNA
<213> ORGANISM: Artificial Sequence
<220> FEATURE:
<223> OTHER INFORMATION: Primer of NST (reverse)

<400> SEQUENCE: 8
ctcacgacat ccaggactga                                              20

<210> SEQ ID NO 9
<211> LENGTH: 20
<212> TYPE: DNA
<213> ORGANISM: Artificial Sequence
<220> FEATURE:
<223> OTHER INFORMATION: Primer of AC3 (forward)

<400> SEQUENCE: 9
tcctgtgttg tgcatacgct                                              20

<210> SEQ ID NO 10
<211> LENGTH: 20
<212> TYPE: DNA
<213> ORGANISM: Artificial Sequence
<220> FEATURE:
<223> OTHER INFORMATION: Primer of AC3 (reverse)

<400> SEQUENCE: 10
```
tcctgtgttg tgcatacgct          20

<210> SEQ ID NO 11
<211> LENGTH: 20
<212> TYPE: DNA
<213> ORGANISM: Artificial Sequence
<220> FEATURE:
<223> OTHER INFORMATION: Primer of OMP (forward)

<400> SEQUENCE: 11
gaagcaggat ggtgsgsssgc          20

<210> SEQ ID NO 12
<211> LENGTH: 20
<212> TYPE: DNA
<213> ORGANISM: Artificial Sequence
<220> FEATURE:
<223> OTHER INFORMATION: Primer of OMP (reverse)

<400> SEQUENCE: 12
atgaggttgg tgaggtcgcg          20

<210> SEQ ID NO 13
<211> LENGTH: 20
<212> TYPE: DNA
<213> ORGANISM: Artificial Sequence
<220> FEATURE:
<223> OTHER INFORMATION: Primer of NCAM (forward)

<400> SEQUENCE: 13
aaaggatggg gaacccatag          20

<210> SEQ ID NO 14
<211> LENGTH: 20
<212> TYPE: DNA
<213> ORGANISM: Artificial Sequence
<220> FEATURE:
<223> OTHER INFORMATION: Primer of NCAM (reverse)

<400> SEQUENCE: 14
taggtgattt tgggctttgc          20

<210> SEQ ID NO 15
<211> LENGTH: 20
<212> TYPE: DNA
<213> ORGANISM: Artificial Sequence
<220> FEATURE:
<223> OTHER INFORMATION: Primer of SOX2 (forward)

<400> SEQUENCE: 15
taggtgattt tgggctttgc          20

<210> SEQ ID NO 16
<211> LENGTH: 20
<212> TYPE: DNA
<213> ORGANISM: Artificial Sequence
<220> FEATURE:
<223> OTHER INFORMATION: Primer of SOX2 (reverse)

<400> SEQUENCE: 16
ttgctgatct ccgagttgtg          20

<210> SEQ ID NO 17
<211> LENGTH: 20
<212> TYPE: DNA

```
<213> ORGANISM: Artificial Sequence
<220> FEATURE:
<223> OTHER INFORMATION: Primer of Ki67 (forward)

<400> SEQUENCE: 17
gcccatcacc acagagattt                                            20

<210> SEQ ID NO 18
<211> LENGTH: 20
<212> TYPE: DNA
<213> ORGANISM: Artificial Sequence
<220> FEATURE:
<223> OTHER INFORMATION: Primer of Ki67 (reverse)

<400> SEQUENCE: 18
cagtcttcag gggctctgtc                                            20

<210> SEQ ID NO 19
<211> LENGTH: 20
<212> TYPE: DNA
<213> ORGANISM: Artificial Sequence
<220> FEATURE:
<223> OTHER INFORMATION: Primer of nestin (forward)

<400> SEQUENCE: 19
gaggaagcat cgaactctgg                                            20

<210> SEQ ID NO 20
<211> LENGTH: 20
<212> TYPE: DNA
<213> ORGANISM: Artificial Sequence
<220> FEATURE:
<223> OTHER INFORMATION: Primer of nestin (reverse)

<400> SEQUENCE: 20
gaggaagcat cgaactctgg                                            20

<210> SEQ ID NO 21
<211> LENGTH: 5
<212> TYPE: PRT
<213> ORGANISM: Artificial Sequence
<220> FEATURE:
<223> OTHER INFORMATION: VGVPG

<400> SEQUENCE: 21

Val Gly Val Pro Gly
1               5

<210> SEQ ID NO 22
<211> LENGTH: 713
<212> TYPE: PRT
<213> ORGANISM: Artificial Sequence
<220> FEATURE:
<223> OTHER INFORMATION: TGPG[VGRGD(VGVPG)6]20WPC

<400> SEQUENCE: 22

Thr Gly Pro Gly Val Gly Arg Gly Asp Val Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Arg Gly Asp Val Gly Val Pro
        35                  40                  45

Gly Val Gly Val Pro Gly Val Gly Val Pro Gly Val Gly Val Pro Gly
    50                  55                  60
```

-continued

```
Val Gly Val Pro Gly Val Gly Val Pro Gly Val Gly Arg Gly Asp Val
 65                  70                  75                  80

Gly Val Pro Gly Val Gly Val Pro Gly Val Gly Val Pro Gly Val Gly
                 85                  90                  95

Val Pro Gly Val Gly Val Pro Gly Val Gly Val Pro Gly Val Gly Arg
            100                 105                 110

Gly Asp Val Gly Val Pro Gly Val Gly Val Pro Gly Val Gly Val Pro
        115                 120                 125

Gly Val Gly Val Pro Gly Val Gly Val Pro Gly Val Gly Val Pro Gly
    130                 135                 140

Val Gly Arg Gly Asp Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Arg Gly Asp Val Gly Val Pro Gly Val Gly Val
            180                 185                 190

Pro Gly Val Gly Val Pro Gly Val Gly Val Pro Gly Val Gly Val Pro
        195                 200                 205

Gly Val Gly Val Pro Gly Val Gly Arg Gly Asp Val Gly Val Pro Gly
    210                 215                 220

Val Gly Val Pro Gly Val Gly Val Pro Gly Val Gly Val Pro Gly Val
225                 230                 235                 240

Gly Val Pro Gly Val Gly Val Pro Gly Val Gly Arg Gly Asp Val Gly
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Arg Gly
        275                 280                 285

Asp Val Gly Val Pro Gly Val Gly Val Pro Gly Val Gly Val Pro Gly
    290                 295                 300

Val Gly Val Pro Gly Val Gly Val Pro Gly Val Gly Val Pro Gly Val
305                 310                 315                 320

Gly Arg Gly Asp Val Gly Val Pro Gly Val Gly Val Pro Gly Val Gly
                325                 330                 335

Val Pro Gly Val Gly Val Pro Gly Val Gly Val Pro Gly Val Gly Val
            340                 345                 350

Pro Gly Val Gly Arg Gly Asp Val Gly Val Pro Gly Val Gly Val Pro
        355                 360                 365

Gly Val Gly Val Pro Gly Val Gly Val Pro Gly Val Gly Val Pro Gly
    370                 375                 380

Val Gly Val Pro Gly Val Gly Arg Gly Asp Val Gly Val Pro Gly Val
385                 390                 395                 400

Gly Val Pro Gly Val Gly Val Pro Gly Val Gly Val Pro Gly Val Gly
                405                 410                 415

Val Pro Gly Val Gly Val Pro Gly Val Gly Arg Gly Asp Val Gly Val
            420                 425                 430

Pro Gly Val Gly Val Pro Gly Val Gly Val Pro Gly Val Gly Val Pro
        435                 440                 445

Gly Val Gly Val Pro Gly Val Gly Val Pro Gly Val Gly Arg Gly Asp
    450                 455                 460

Val Gly Val Pro Gly Val Gly Val Pro Gly Val Gly Val Pro Gly Val
465                 470                 475                 480

Gly Val Pro Gly Val Gly Val Pro Gly Val Gly Val Pro Gly Val Gly
```

-continued

```
                    485                 490                 495
Arg Gly Asp Val Gly Val Pro Gly Val Gly Val Pro Gly Val Gly Val
                500                 505                 510

Pro Gly Val Gly Val Pro Gly Val Gly Val Pro Gly Val Gly Val Pro
            515                 520                 525

Gly Val Gly Arg Gly Asp Val Gly Val Pro Gly Val Gly Val Pro Gly
        530                 535                 540

Val Gly Val Pro Gly Val Gly Val Pro Gly Val Gly Val Pro Gly Val
545                 550                 555                 560

Gly Val Pro Gly Val Gly Arg Gly Asp Val Gly Val Pro Gly Val Gly
                565                 570                 575

Val Pro Gly Val Gly Val Pro Gly Val Gly Val Pro Gly Val Gly Val
            580                 585                 590

Pro Gly Val Gly Val Pro Gly Val Gly Arg Gly Asp Val Gly Val Pro
        595                 600                 605

Gly Val Gly Val Pro Gly Val Gly Val Pro Gly Val Gly Val Pro Gly
    610                 615                 620

Val Gly Val Pro Gly Val Gly Val Pro Gly Val Gly Arg Gly Asp Val
625                 630                 635                 640

Gly Val Pro Gly Val Gly Val Pro Gly Val Gly Val Pro Gly Val Gly
                645                 650                 655

Val Pro Gly Val Gly Val Pro Gly Val Gly Val Pro Gly Ala Ala Ala
            660                 665                 670

Val Gly Arg Gly Asp Ala Val Gly Val Pro Gly Val Gly Val Pro Gly
        675                 680                 685

Val Gly Val Pro Gly Val Gly Val Pro Gly Val Gly Val Pro Gly Val
    690                 695                 700

Gly Val Pro Gly Ala Ala Trp Pro Cys
705                 710
```

SPHEROID CULTURE METHOD FOR NEURAL STEM CELL

TECHNICAL FIELD

The present invention relates to a method for culturing neural stem cells into spheroids, the method including culturing the neural stem cells in a culture vessel coated with a protein including a VGVPG pentapeptide (SEQ No. 21) and an RGD integrin receptor ligand.

BACKGROUND ART

A spheroid culture method is a method of culturing cells into spheroids, and is mainly used for preservation and proliferation of stem cells. Cell spheroid culture methods include a liquid overlay technique, a hanging drop technique, a microwell hanging drop technique, a microwell array from micropatterned agarose wells, and microfluidic spheroid formation (Rivron, N C et al. (2012) Tissue deformation spatially modulates VEGF signaling and angiogenesis. Proc. Natl. Acad. Sci. USA 109, 6886-6891).

However, since the previously developed spheroid culture methods are physical means, stability and reproducibility during spheroid formation are poor. Accordingly, there has been a demand for a spheroid culture method capable of increasing the stability and viability of cells during spheroid culture.

DISCLOSURE

Technical Problem

Under this background, the present inventors have completed a spheroid culture method for neural stem cells using an extracellular matrix recombinant protein in order to overcome the limitations of the existing physical spheroid culture technology.

Technical Solution

The present invention provides a method for culturing neural stem cells into spheroids, the method including culturing the neural stem cells in a culture vessel coated with a protein containing a VGVPG pentapeptide (SEQ No. 21) and an RGD integrin receptor ligand.

Advantageous Effects

A spheroid culture method for neural stem cells using a protein including a VGVPG pentapeptide (SEQ No. 21) and an RGD integrin receptor ligand according to an aspect of the present invention can stably form neural stem cells into spheroids compared to the conventional physical spheroid culture method.

The neural stem cells cultured by the above method have minimized changes in their cell characteristic, and thus can stably maintain the cell function.

In addition, since the neural stem cells cultured by the above method can be stored frozen, the storage period of the neural stem cells is extended and thus can be utilized in various fields.

BEST MODE FOR CARRYING OUT THE INVENTION

Figure 1:
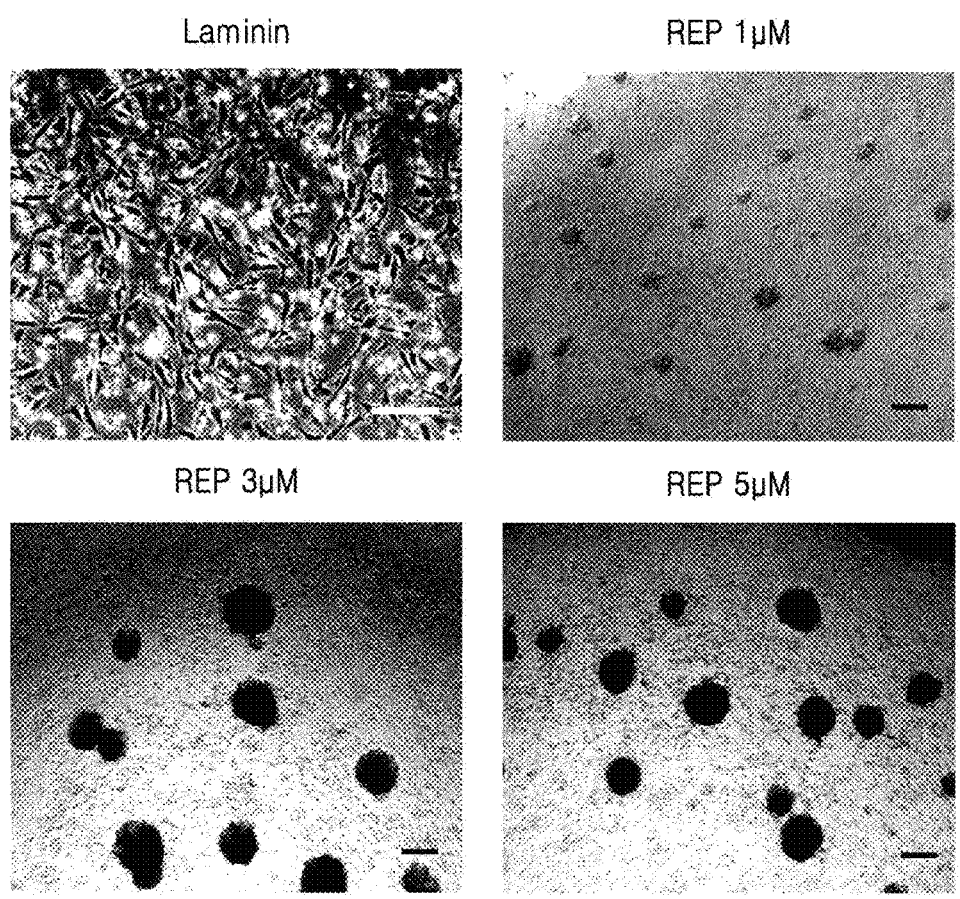
FIG. 1 shows contrast microscopic images of ORN progenitor cells on plates pretreated with laminin and REP for 24 hours.

One embodiment of the invention provides a method of culturing neural stem cells into spheroids, the method including: culturing neural stem cells in a culture vessel coated with a protein including a VGVPG pentapeptide (SEQ No. 21) and an RGD integrin receptor ligand; and isolating the neural stem cells that are aggregated and formed into spheroids during the culturing.

The protein is obtained by recombining a part of elastin, which is well known as an extracellular matrix. The recombinant protein may interact with an integrin on the cell surface to activate a signaling system of a cultured cell. Through this, neural stem cells can be cultured into stable spheroids. The recombinant protein may be composed of TGPG[VGRGD(VGVPG)$_6$]$_{20}$WPC (SEQ No. 22). The recombinant protein may be obtained by producing a protein gene encoding TGPG[VGRGD(VGVPG)$_6$]$_{20}$WPC (SEQ No. 22) through recursive directional ligation in a plasmid from the monomer gene of seven pentapeptides, VGRGD (VGVPG)$_6$, and expression and purification of the protein gene in transformed cells. As used herein, the term 'protein' may be used interchangeably with 'polypeptide'.

The protein may be coated on the culture vessel at a concentration of 1 to 10 μM, specifically, 1 to 8 μM, more specifically, 1 to 5 μM. The present inventors have discovered that, spheroids can be stably formed in the case of culturing neural stem cells in a culture vessel coated with the recombinant protein at concentrations of 1 μM, 3 μM and 5 μM, respectively, compared to a culture vessel coated with laminin.

The neural stem cells are capable of self-renewal and refer to cells having the capability to differentiate into cells of a nervous system, and the cells can be differentiated into neurons, astrocytes, or oligodendrocytes. As used herein, the term 'neural stem cell' may be used interchangeably with 'neural precursor cell' or 'neural progenitor cell'.

The neural stem cells or neural progenitor cells may be derived from embryonic stem cells isolated from early embryos of mammals, embryonic germ cells isolated from primordial germ cells of an embryonic period, multipotent adult progenitor cells isolated from adults, and induced pluripotent stem cells artificially created by induction of adult somatic cells, which are non-pluripotent cells, by artificially expressing particular genes. The pluripotent adult stem cells may be derived from adult tissues or blood such as umbilical cord blood, bone marrow, fat or brain tissues. In addition, the above embryonic stem cells, embryonic germ cells, adult stem cells, and induced pluripotent stem cells may include stem cells produced by transfection of genes into these cells or substitution or fusion of cell nucleus.

The neural stem cells may be olfactory receptor neuronal precursor cells. The present inventors have discovered that the olfactory receptor neuronal precursor cells can be stably cultured into spheroids in a culture vessel coated with the protein composed of TGPG[VGRGD(VGVPG)$_6$]$_{20}$WPC (SEQ No. 22).

The "spheroid" is a small 'spheroidal' body made through tertiary tissue culture, and the spheroid is a kind of small tissue, which may have different functions by dividing into inside and outside parts, and has a shape that mimics a functional unit of tissue. The spheroid cultured cells are similar with animal or human tissues in their intrinsic shapes and properties, and the spheroid culture is being developed as a platform for a research applying them. As used herein, the term 'spheroid' may be used interchangeably with 'spherical'.

The step of culturing collectively refers to activities of culturing cells isolated from an organism or the like, and may include primary culture or sub-culture. In the cell culture method, all known methods that are commonly used may be applied.

The step of culturing may be subculture. The subculture is one of the cell proliferation methods, and refers to a method in which cells to be cultured are periodically transplanted into a new culture medium to continue the generation of cells. Even during the subculture, stemness of neural stem cells can be maintained. The present inventors have discovered that the stemness is maintained by discovering that SOX2, Ki67, and nestin which are specific marker genes of neural stem cells are normally expressed in neural stem cells cultured into spheroids on day 10.

The method may further include primary culture of the neural stem cells before the step of culturing. The primary culture refers to direct culturing of cells, tissues or organs isolated from living organisms as a material. Specifically, it refers to the culture prior to subculture. The present inventors have discovered that rat olfactory receptor neural progenitor cells were primary cultured, and then the primary cultured neural progenitor cells can be formed into spheroids by culturing them in a culture vessel coated with the protein.

The culturing process may be performed in a suitable medium under culturing condition known in the art, and may be easily adjusted according to selected neural stem cells by those skilled in the art. The cultivation temperature may be 35° C. to 40° C., specifically 36° C. to 39° C., and more specifically 37° C. to 38° C. As the medium, a conventional stem cell culture medium such as DMEM/F12 medium, KO-DMEM/F12 medium, etc. may be used for stem cells. Specifically, a medium containing FBS, penicillin streptomycin, kanamycin, gentamicin, and the like may be used.

The seeding in the culture vessel may include all the activities performed to culture the neural stem cells in the culture vessel, such as adding neural stem cells to the culture vessel, or adhering the neural stem cells to the culture vessel. In the step of culturing, the neural stem cells may be seeded at a cell concentration of $1 \times 10^4$ to $1 \times 10^8$ cells/ml, specifically $1 \times 10^5$ to $1 \times 10^7$ cells/ml, and more specifically, $1 \times 10^6$ to $1 \times 10^7$ cells/ml.

In the step of culturing, the neural stem cells may be aggregated to form spheroids. The time for culturing the neural stem cells to aggregate to form spheroids is not particularly limited thereto, but may be 1 hour to 24 hours, specifically 1 hour to 18 hours, and more specifically 1 hour to 12 hours. The present inventors have discovered that in the case that the neural stem cells are cultured in a culture vessel coated with the protein, the neural stem cells can aggregate to form spheroids within 24 hours.

In addition, the diameter of the formed spheroid may be 50 to 80 μm, specifically 55 to 75 μm, and more specifically 60 to 70 μm. The present inventors have discovered that neural stem cells cultured on a plate coated with the 3 μM and 5 μM recombinant protein form spheroids, and the mean diameter of the formed spheroids is maintained at 60 to 70 μm for 10 days.

The method may further include cryopreservation of the neural stem cells and thawing the cryopreserved neural stem cells. The cryopreservation refers to stably maintaining cells or tissues over a long period of time through freezing. The cells generally experience a mutation rate of about one in 10,000 cultured cells, and if sub-culture of the cells is continued for a long period of time, they may change into a cell population of different characters from the original cell population. In severe cases, the unique function of the cells may disappear by the continued sub-culture. Also, they may be infected with mycoplasma or the like during the subculture. In particular, in the case of stem cells, in order to use them as therapeutic agents, healthy stem cells must be immediately available in a necessary situation, so a method for effectively freezing and preserving the stem cells is required. The cryopreservation can be performed to freeze and preserve cells or tissues before the intrinsic properties of the cells or tissues are lost and use them when necessary.

As a result of testing physiological functions of differentiated neural cells by cryopreserving and thawing neural stem cells cultured into spheroids, the present inventors discovered that there were little changes in the physiological function of the neural cells even if the storage period of the progenitor cell state is extended.

MODE FOR CARRYING OUT THE INVENTION

Hereinafter, it will be described in more detail through exemplary embodiments. However, these exemplary embodiments are only for illustrating the present disclosure, and the scope of the present invention is not limited to these exemplary embodiments.

Example 1: Spheroid Culture of Neural Stem Cells 1-1. Primary Culture of Olfactory Receptor Neural Progenitor Cells Primary culture of rat olfactory receptor neuron (ORN) progenitors by modifying some of the known culture methods (Ronnett G V, Hester L D, Snyder S H (1991) J Neurosci 11 (5): 1243-55) was performed.

Specifically, 0 to 1 day old rats were beheaded, and the olfactory epithelium was dissected and immediately placed in the modified Eagle's medium (MDV, Welgen Inc., Worcester, USA) containing D-valine containing 4.8 g/L of HEPES buffer. The turbinates were transferred to fresh MDV medium to minimize contamination and centrifuged at 1000 rpm for 5 minutes. After decanting the supernatant, the tissue was chopped to obtain fragments of about 0.5 mm, resuspended in MDV medium and centrifuged at 1000 rpm for 5 minutes. Minced tissues were placed in 30 ml MDV medium containing 1% (w/v) BSA (SIGMA, St. Louis, USA), 1 mg/ml hyaluronidase (SIGMA), 50 µg/ml DNase (SIGMA), 2 mg/ml collagenase D (Roche Diagnostics GmbH, Mannheim, Germany), and 5 mg/ml dispase II (Roche), and cultured at 37° C. for 1 hour. After culture, cells were passed through 150 µm wire mesh and nylon mesh filters (70 µm, 40 µm and 10 µm. Small Parts, Miami, FL). After centrifugation at 1200 rpm for 5 min, the cell pellet was resuspended in MDV medium containing 10% (v/v) fetal bovine serum (FBS; GIBCO, USA), 5% (v/v) Nu-serum (BD Biosciences, Franklin Lakes, NJ, USA), 10 UM cytosine arabinoside (ara C), and 25 ng/ml nerve growth factor (NGF, Collaborative Research). Cultures were placed in a humidified 37° C. culture incubator containing 5% $CO_2$ and the cells were fed with modified Eagle's medium containing D-valine, 15% FBS, gentamicin, kanamycin and ara C (SIGMA).

1-2. Comparison Between Spheroid Culture in a Vessel Coated with a Recombinant Protein and Culture in a Vessel Coated with Laminin For a comparison between the culture in a vessel coated with a recombinant protein (REP, TGPG[VGRGD (VGPVPG)$_6$]$_{20}$WPC) and culture in a vessel coated with laminin in whether neural stem cells are cultured into spheroids, the rat ORN progenitor cells primary cultured in Example 1-1 above were plated on REP-coated or laminin-coated cell culture plates.

Specifically, before plating the isolated ORN progenitor cells, 96-well plates (Thermo Scientific, Waltham, USA) were coated with 100 µl of 3 µM REP diluted with PBS, and they were cultured in the humidified 37° C. culture incubator containing 5% $CO_2$ for 1 hour. The REP was prepared by the previously described method (Jeon W B, Park B H, Wei J, Park R W (2011) J Biomed Mater Res A 97 (2): 152-7). After culturing for 1 hour in the humidified incubator, the REP solution was aspirated, and $1 \times 10^6$ cells/ml of the isolated ORN progenitor cell suspension was placed and stored in the humidified incubator. MEM medium (Welgene, Gyeongsan, Republic of Korea) containing fresh 0.5% FBS (GE Healthcare lifesciences, Brussel, Belgium), 0.5% penicillin streptomycin (Thermo Fisher, Waltham, USA), kanamycin (SIGMA), and gentamicin (SIGMA) was replaced every 24 hours.

As a result, as shown in FIG. 1, when cultured on the plate coated with REP, ORN progenitor cells were aggregated within 24 hours to form spheroids, but when cultured on the plate coated with laminin, neurites outgrowth occurred and the cells were differentiated without spheroid culture.

Next, in order to check the optimal conditions for spheroid formation, the diameter and shape of the spheroids were observed according to the seeding populations and the concentration of REP by measuring the diameter of the formed spheroids.

Figure 2:
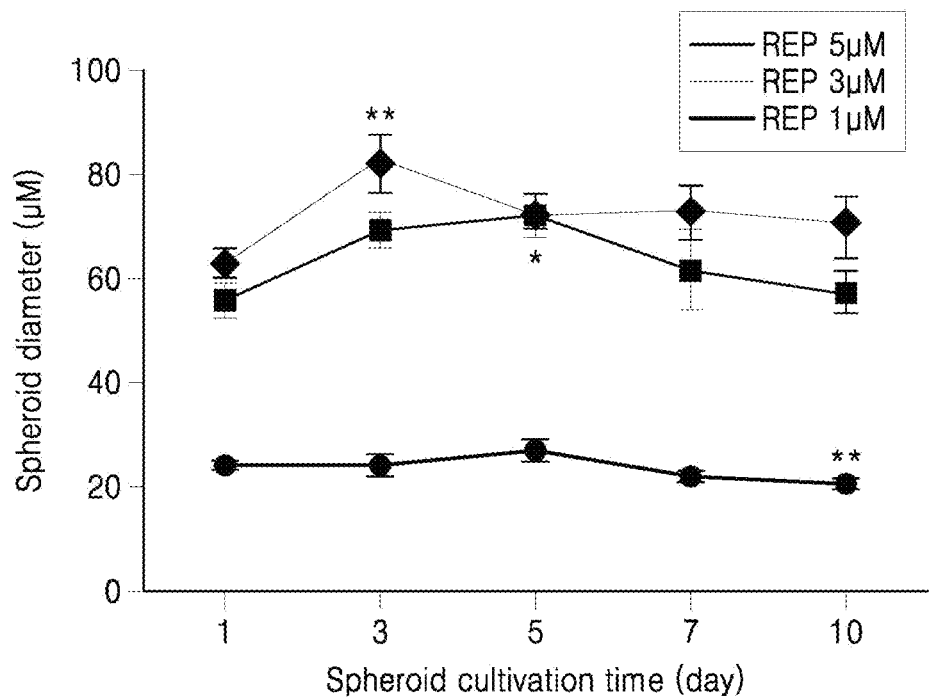
FIG. 2 is a plot showing the change in the diameter of spheroids according to cultivation time. (*<0.05, <0.01, *<0.001)

As a result, as shown in FIG. 2, 24 hours after cell inoculation, the mean diameters of spheroids on the plates coated with 1 µM REP, 3 µM REP, and 5 µM REP were 24.2±0.7 µm, 62.6±2.2 µm, and 56.2±2.8 µm, respectively. On the 3rd day, the mean diameter of the spheroids on the plate coated with 3 µM REP significantly increased to 77.5±3.3 µm, and on the 5th day, the mean diameter of the spheroids on the plate coated with 5 µM REP significantly increased to 69.4±3.6 µm. In addition, the mean diameter of the ORN progenitor cell spheroids on the plate coated with 3 µM and 5 µM REP was 60 to 70 µm, which was maintained for 10 days. However, the spheroid diameter of the ORN progenitor cells on the plate coated with 1 µM REP was approximately 20 µm and they showed unstable spheroid morphology and cell aggregation. This is because the relatively small diameter of the spheroids on the plate coated with 1 µM REP may result in a small population of neural cells after differentiation, and the ability to generate electrical signals in response to odor stimulation is limited. Therefore, in subsequent experiments, REP was used at the concentration of 3 µM.

1-3. Demonstration of Effects of the Recombinant Protein on Spheroid Culture

In order to determine effects of the REP on spheroid formation, surface properties of REP-coated coverslips were observed using atomic force microscopy (AFM) and scanning electronic microscopy (SEM).

Specifically, for AFM and SEM image observation, glass coverslips were coated with 3 µM REP and 25 µg/ml laminin. To coat the coverslip with REP, 3 µM REP solution was poured onto the coverslip and incubated at 37° C. for 1 hour. Thereafter, the coverslip was washed three times with warmed autoclaved distilled water at 37° C. and dried in a hood. To prepare a laminin-coated coverslip, 25 µg/ml laminin was diluted with autoclaved distilled water and poured over the coverslip and the coverslip was stored at 37° C. overnight. Thereafter, the coverslip was washed three times with pressurized distilled water and dried with a critical point dryer (EM CPD 300; Leica, Wetzlar, Germany). AFM (XE-150; Park Systems, Suwon, Republic of Korea) was performed in non-contact mode with a scanning speed of 0.5 Hz. Before SEM observation, the coverslip was coated with osmium (Osmium plasma coater, Vacuum Devices Inc., Mito, Japan), and SEM was performed at a chamber pressure of 6.5$^{-6}$ mbar.

Figure 3:
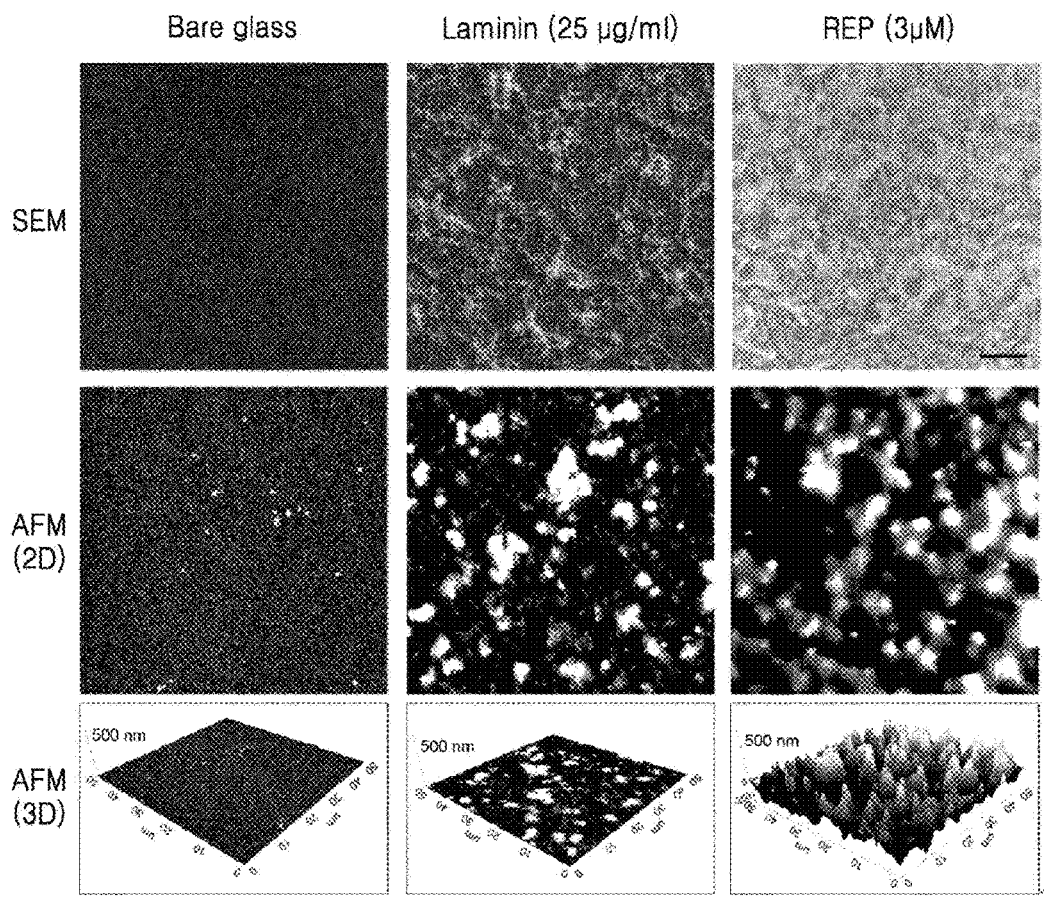
FIG. 3 shows SEM and AFM images of untreated glass (Bare glass), cover glass coated with 3 μM REP, and cover glass coated with 25 μg/ml laminin, respectively. The magnification of the SEM images is 1000×, and the scale bar is 50 μm.

As a result, as shown in FIG. 3, REP formed a tissue-like porous structure and combined with the laminin matrix to form a network-like structure.

Figure 4:
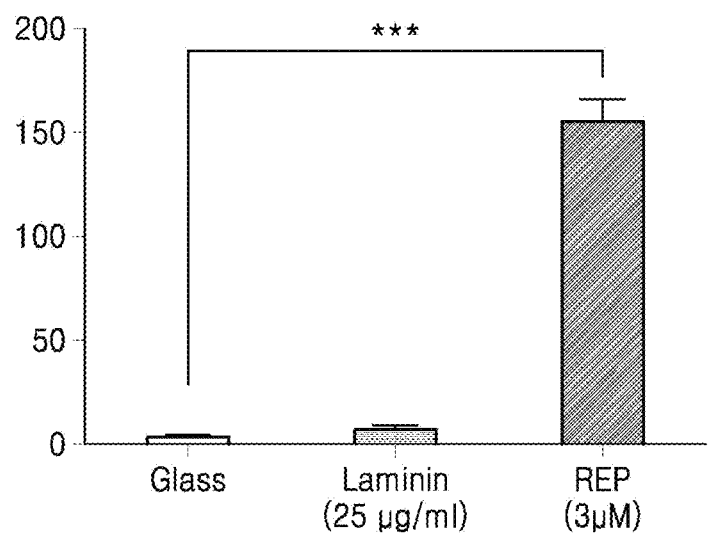
FIG. 4 is a diagram showing comparison of roughness of untreated glass, cover glass coated with 3 M REP, and cover glass coated with 25 μg/ml laminin. (***<0.001)

In addition, as shown in FIG. 4, as a result of observing the surface topography and roughness using AFM, compared with laminin, REP formed a structure with a height of hundreds of nano-units and had roughness of 148.3±15.9 nm. The surface structure of REP had significantly higher height and roughness, which was 23.8 times higher than the structure generated from the laminin-coated surface.

Therefore, since the porous structure of REP with relatively high roughness can affect cell adhesion, it can be determined that the different topographical properties of REP compared to laminin affect the spheroid formation of ORN progenitors in the REP-coated plate.

Example 2: Evaluation of Cell Viability of Spheroid Cultured Neural Stem Cells Since it is essential for neural stem cells to maintain cell viability while cultured into spheroids, a calcein assay was performed to evaluate the viability of ORN progenitor cells cultured into spheroids according to the cultivation time.

Specifically, calcein assay reagent (calcein red-orange, AM; Invitrogen, Carlsbad, USA) is used to evaluate cell viability. Spheroid ORN progenitor cells were washed three times with Dulbecco's phosphate-buffered saline (DPBS; Gibco® by Life Technologies™, Waltham, USA), treated with 3 μM calcein-AM solution, and cultivated at 37° C. for 30 minutes. Cell viability in each well was quantified by measuring optical density at 517 nm with a fluorescence reader (Gemini EM; Molecular Devices, San Jose, USA). The total $OD_{517nm}$ value was normalized to the value measured in spheroid ORN progenitor cells on the first day, and the decrease in fluorescence intensity indicates decrease in viability according to environmental conditions and cell loss according to changes of culture media.

Figure 5:
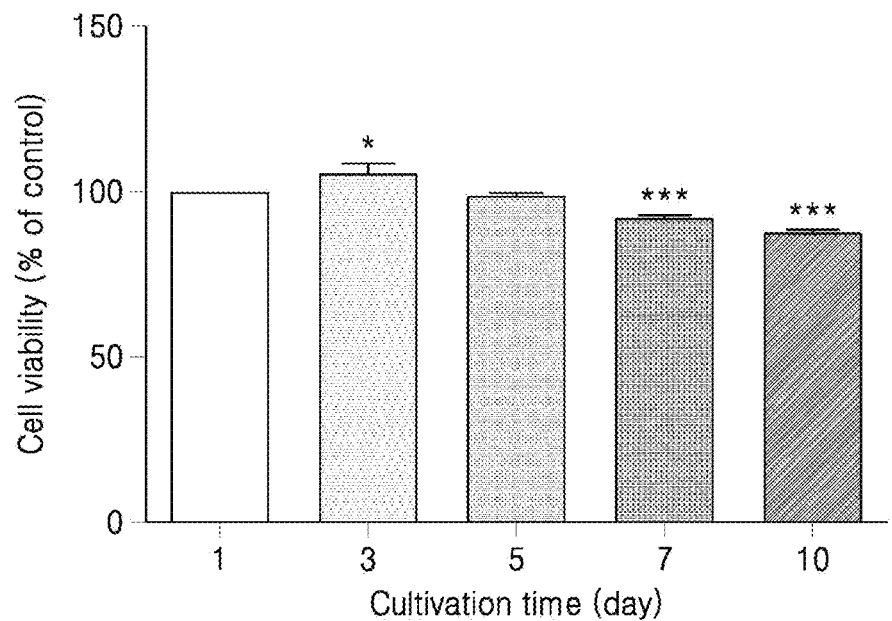
FIG. 5 is a diagram showing cell viability of spheroid ORN progenitor cells formed on a plate coated with 3 μM REP according to cultivation time. (n=6, *<0.05, ***<0.001)

As a result, as shown in FIG. 5, the fluorescence intensity was significantly increased by 1.05±0.03 times on the 3rd day, and the viability gradually decreased after 3 days, and slightly decreased to 0.087±0.01 times on the 10th day, but it was determined that the spheroid ORN progenitor cells showed sufficient viability for about 10 days.

Example 3: Evaluation of Stemness of Spheroid Cultured Neural Stem Cells

In order to evaluate whether the spheroid-cultured ORN progenitor cells maintain a stemness, mRNA levels of stem cell markers were analyzed by quantitative real-time polymerase chain reaction (qRT-PCR). SOX2, Ki67, and nestin were used as specific marker genes for neural stem cells. Neuron-specific enolase (NSE) was used as a gene to demonstrate that no differentiation of spheroid-cultured ORN progenitors occurred.

Specifically, total RNA was obtained from spheroid ORN progenitors using Trizol (Trizol® Reagent; Life technologies, Waltham, USA), and cDNA was synthesized by reverse transcription. qRT-PCR was performed under conditions of 40-45 repetitions at 95° C. for 30 sec, at 60° C. for 30 sec, and at 72° C. for 30 sec using a SYBR Green PCR Master Mix Kit (QuantiTect® SYBR® Green PCR Kit; QIAGEN, Hilden, Germany) on a Rotor-Gene Q (QIAGEN, Hilden, Germany). Primers of the sequences shown in Table 1 were purchased from GenoTeck (Daejeon, Korea) and Bionics (Daejeon, Korea). The housekeeping gene cyclophilin A was used as an internal standard.

TABLE 1

| Name | Direction | Sequence |
|---|---|---|
| cyclophilin A | Forward | AGC ACT GGG GAG AAA GGA TT |
| | Reverse | AGC CAC TCA GTC TTG GCA GT |
| MAP2 | Forward | TGT TGC TGC CAA GAA AGA TG |
| | Reverse | ACG TGG CTG GAC TCA ATA CC |
| NSE | Forward | GTG GAC CAC ATC AAC AGC AC |
| | Reverse | TGA GCA ATG TGG CGA TAG AG |
| Neuron-specific class III beta-tubulin | Forward | TGA GGC CTC CTC TCA CAA GT |
| | Reverse | CTC ACG ACA TCC AGG ACT GA |
| Adenyl cyclase III | Forward | TCC TGT GTT GTG CAT ACG CT |
| | Reverse | ACG TTA GCC AGG ATC TCC CT |
| olfactory marker protein (OMP) | Forward | GAA GCA GGA TGG TGS GSS GC |
| | Reverse | ATG AGG TTG GTG AGG TCG CG |
| Neuronal Cell Adhesion Molecule (NCAM) | Forward | AAA GGA TGG GGA ACC CAT AG |
| | Reverse | TAG GTG ATT TTG GGC TTT GC |
| SOX2 | Forward | AGG GCT GGG AGA AAG AAG AG |
| | Reverse | TTG CTG ATC TCC GAG TTG TG |
| Ki67 | Forward | GCC CAT CAC CAC AGA GAT TT |
| | Reverse | CAG TCT TCA GGG GCT CTG TC |
| Nestin | Forward | GAG GAA GCA TCG AAC TCT GG |
| | Reverse | CAG CTT TAG CTT GGG ATT GC |

Figure 6:
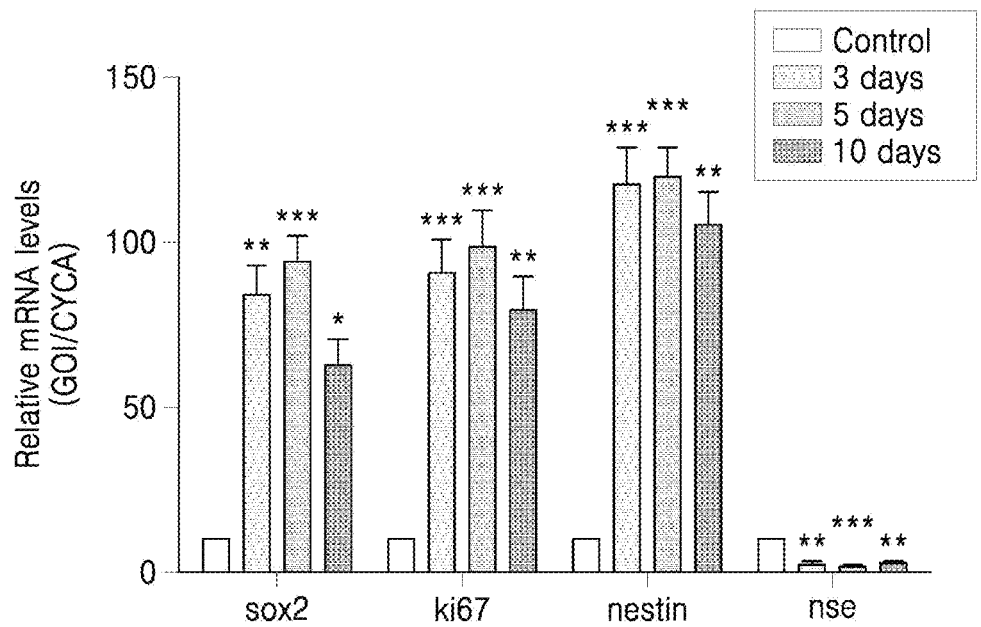
FIG. 6 is a diagram comparing expression levels of stem cell markers in a control group (ORN on laminin-coated plates) and spheroid ORN cell groups (ORNs on REP-coated plates on Days 3, 5, and 10).

As a result, as shown in FIG. 6, the normalized relative mRNA levels of SOX2, Ki67 and nestin on day 3 were 8.4±0.8-fold, 8.6±0.8-fold, and 11.7±1.1-fold, respectively. The expression levels of the three markers were slightly increased on day 5. At day 10, the expression level was lower than that at day 3, but these changes were not statistically significant. In addition, NSE expression increased approximately 0.1-fold on days 3, 5 and 10, and was hardly expressed. In other words, it was determined that the spheroid cultured ORN progenitor cells normally express the neural stem cell-specific marker, and since differentiation did not occur, the stemness is maintained normally. Then, in order to further determine the stemness of the spheroid ORN progenitor cells, immunocytochemistry (ICC) was performed using stemness markers SOX2, Ki67, and nestin.

Specifically, the medium was aspirated and the cells were washed with PBS. Cells were fixed with a 1:1 mixture of acetone and methanol. The cells were infiltrated by cultivation in 0.05% Triton X-100 (Triton® X-100; SIGMA, St. Louis, USA) for 10 minutes, and blocked with 4% normal donkey serum for 1 hour. Thereafter, the cells were cultured overnight at 4° C. in primary antibody dilution solution. As primary antibody, 1 μg/ml anti-NST (abcam, Boston, USA), 1:100 anti-NCAM (AB5032, abcam), 1:200 anti-microtubule associated protein 2 (4542, Cell signaling Technology, Danvers, USA), 1:200 anti-SOX2 (sc17320, Santa Cruz, Dallas, USA), 1:200 anti-nestin (MAB353, Millipore Corp. Burlington, USA), and 1:200 anti-Ki67 (D3B5, Cell Signaling Technology) antibody was used. The cultured cells were washed 3 times with PBS and fluorescently labeled with secondary antibody for 2 hours at room temperature. As the secondary antibody, donkey anti-mouse IgG H&L Alexa Fluor®488 (ab150105; abcam), goat anti-rabbit IgG H&L Alexa Fluor®568 (ab175471; abcam), and donkey anti-goat IgG H&L Alexa Fluor®488 (ab150129; abcam) was used. After washing with PBS, the cells were immersed in an encapsulant containing DAPI (VECTOR, Burlingame, USA) and Hoechst (Invitrogen, Carlsbad, USA) and sealed with coverslips. Fluorescence images were acquired using a confocal microscope (Zeiss LSM 700; Carl Zeiss, Obekochen, Germany).

Figure 7:
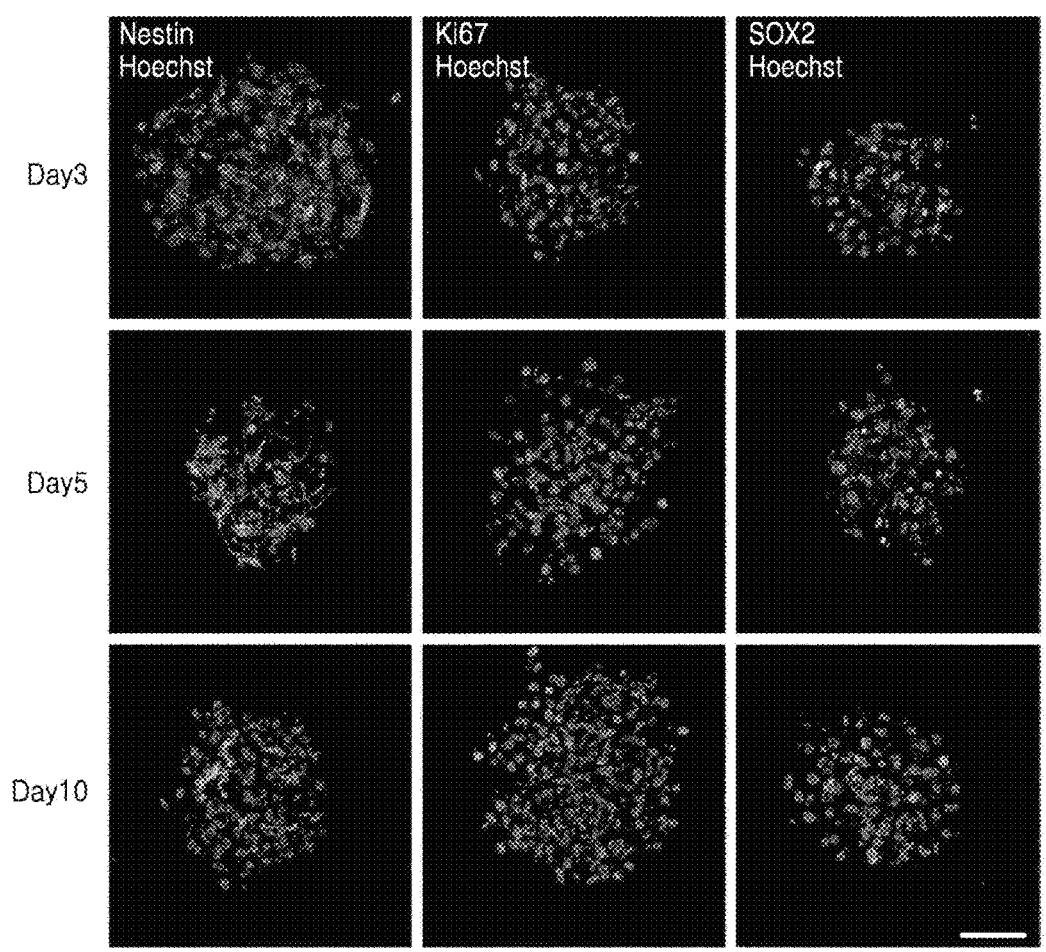
FIG. 7 shows immunocytochemical images of stem cell-related markers in a spheroid ORN cell group. The scale bar is 50 μm.

As a result, as shown in FIG. 7, nestin was expressed on the surface of ORN progenitor cell spheroids, Ki67 was co-labeled in the nucleus, and SOX2 was expressed in the neuronal cell body. There was no significant change in these expression characteristics. Although the expression pattern decreased with the cultivation time, it was determined that the neural stem cell-specific marker gene was still normally expressed on the 10th day.

Figure 8:
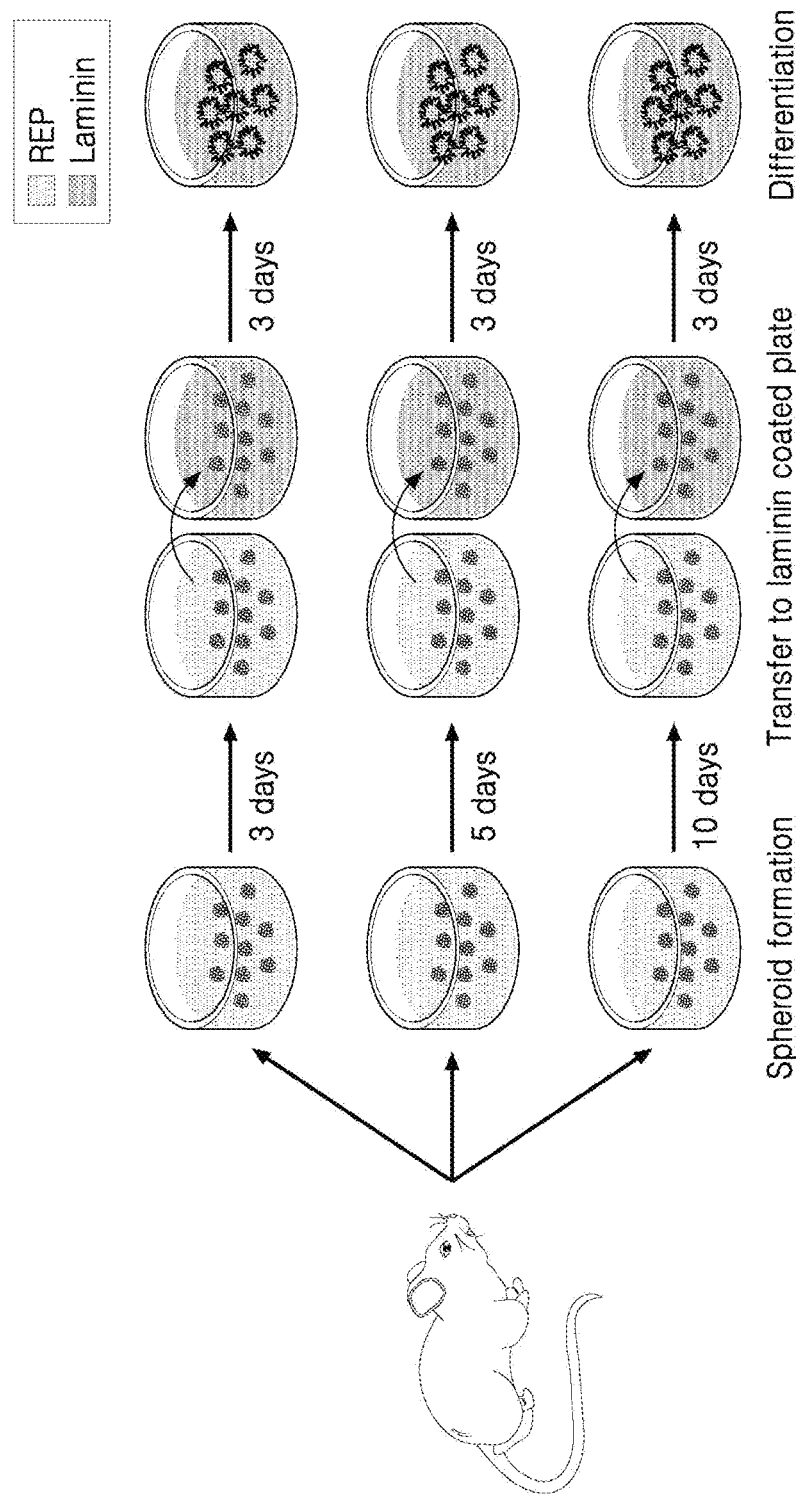
FIG. 8 is a diagram illustrating a differentiation process of ORN progenitor cells cultured into spheroids.

Example 4: Demonstration of Differentiation Capacity of Spheroid-Cultured Neural Stem Cells Spheroid ORN progenitor cells were differentiated and their developmental characteristics were monitored using qPCR and ICC. As shown in FIG. 8, the spheroid ORN progenitor cells were transferred to a laminin-coated plate and cultured for 72 hours to perform differentiation of the spheroid ORN progenitor cells.

Figure 9:
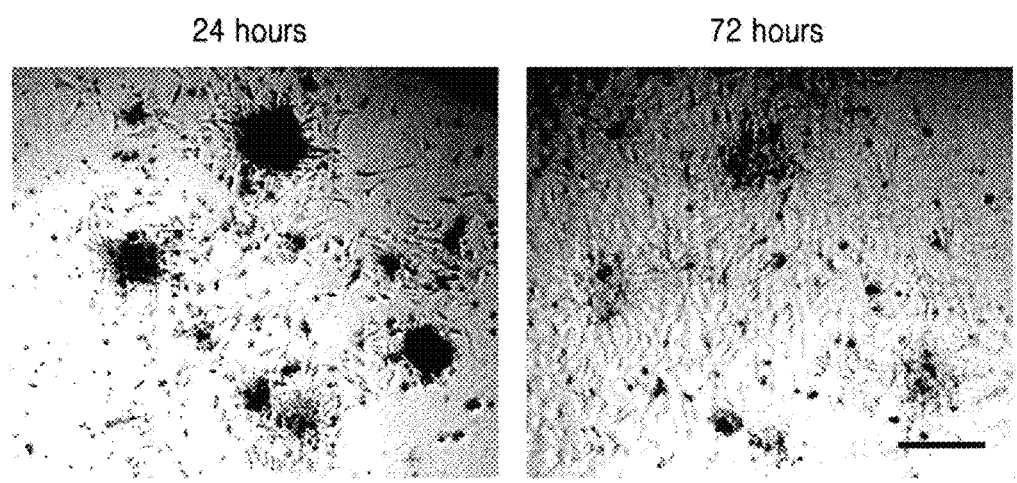
FIG. 9 shows microscopic images of spheroid ORN cells cultured for 72 hours on a plate coated with laminin. The scale bar is 100 μm.

As a result, as shown in FIG. 9, in the case that the spheroid ORN progenitor cells were transferred to the laminin-coated plate, the spheroid ORN progenitor cells migrated radially and exhibited axon generation.

Next, in order to analyze the differentiation of spheroid ORN progenitor cells in-depth, the transcriptional levels of ORN developmental markers such as ac3, omp, map2 and ncam, were analyzed by qPCR. Adenyl cyclase III (AC3), an important protein in the ORN, plays an important role in the olfactory signaling cascade. Olfactory marker protein (OMP) is also a protein found in fully matured ORNs. Microtubule associated protein 2 (MAP2) and NSE are expressed in differentiated neurons. Therefore, these markers were used as neuronal maturation markers. Neural cell adhesion molecule (NCAM) was used as a neural cell marker.

Figure 10:
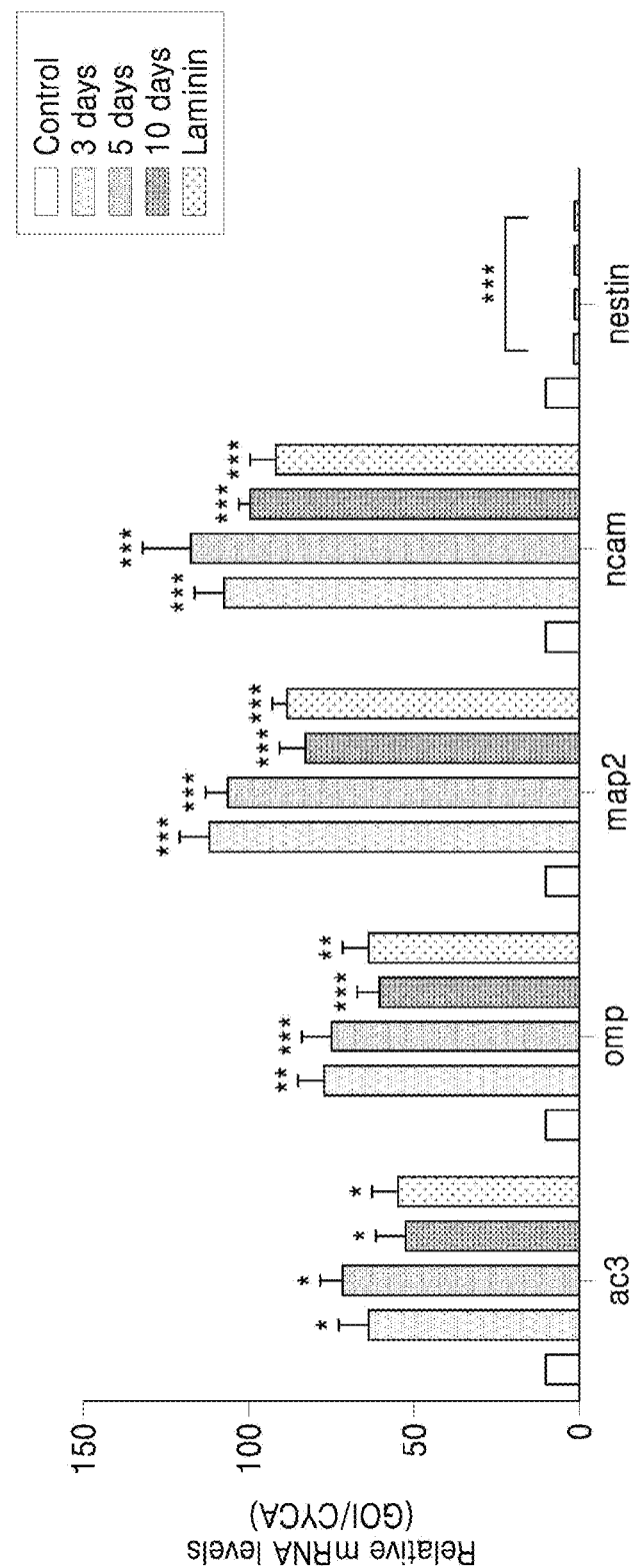
FIG. 10 is a diagram showing results of qPCR analysis for ORN development markers in spheroid ORN cells according to cultivation time.

As a result, as shown in FIG. 10, the expression levels of ac3, omp, map2, and nse on day 3 were 6.3±0.7, 6.3±0.7, 8.7±0.5, and 9.1±0.8 fold, respectively. On day 5, the expression levels of ac3 and ncam increased, and the expression levels of omp and map2 decreased. At day 10, the expression levels of all markers decreased compared to the level at day 3. In contrast, the expression level of nsetin on days 3, 5 and 10 in the laminin group was about 0.1-fold, indicating that spheroid ORN progenitor cell differentiation did not occur.

Figure 11:
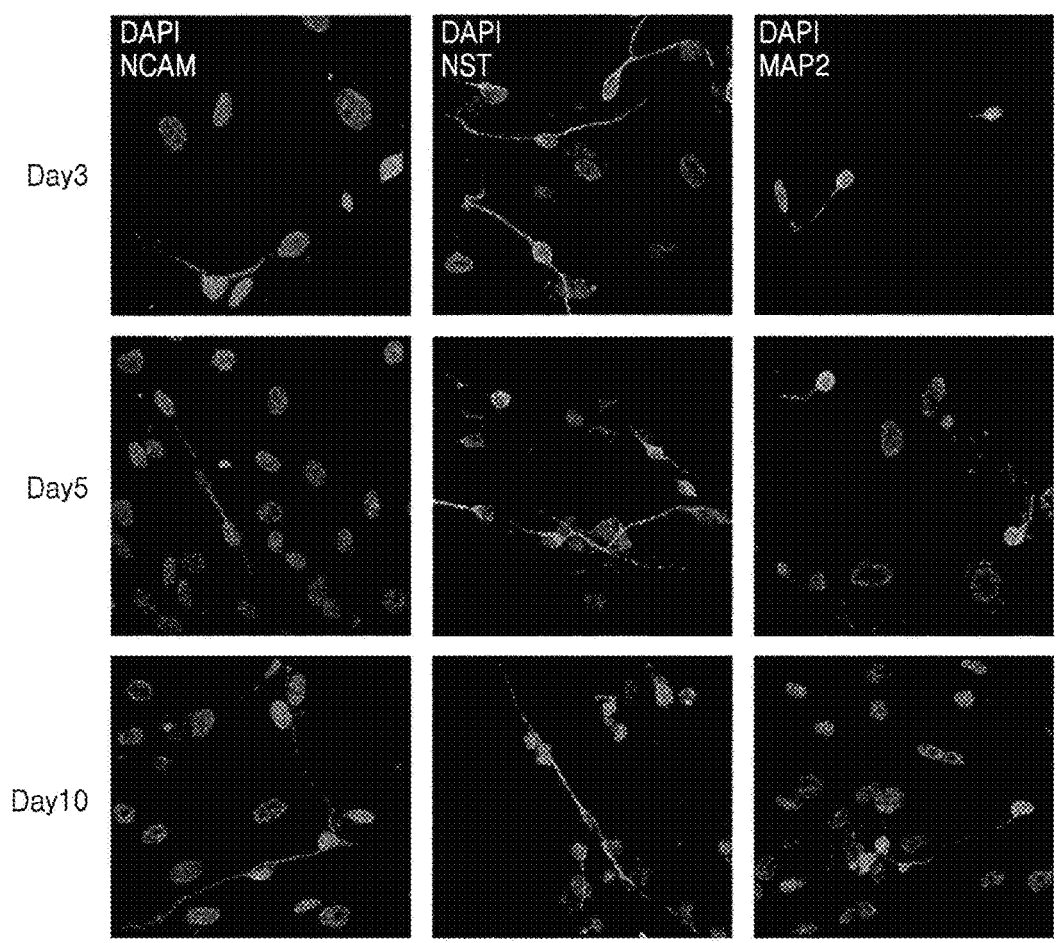
FIG. 11 shows results of immunocytochemical analysis using anti-NST, anti-NCAM, and anti-MAP2 to confirm differentiation of ORN cells cultured for 72 hours. The scale bar is 50 μm.

To more clearly determine the differentiation of spheroid ORN progenitor cells, cells were immunostained with βIII-tubulin (NST), NCAM and MAP2 expressed in ORN. As a result, as shown in FIG. 11, immunostaining of ORN using an antibody against NST and NCAM protein showed that they were clearly expressed in neurites and neuronal cell bodies (soma) of ORN. In addition, MAP2 expression was observed only in one neurite in bipolar neurons. That is to say, the above results indicate that the spheroid ORN progenitor cells can be differentiated into bipolar neurons, which are unique characteristics of ORN in vivo.

Example 5: Determination of Physiological Characteristics of Neural Cells Differentiated from Spheroid Cultured Neural Stem Cells

5-1. Determination of Activity by Deodorant Stimulation

To facilitate comparison with in vivo ORNs, the physiological properties of ORNs were validated using calcium imaging assays. The activity of the spheroid-cultured ORN progenitor cells was evaluated by transferring them to the laminin-coated plates, and measuring the change in fluorescence intensity by stimulating ORN activity with a mixture of odorant. In addition, the total-calcium concentration and response rate stimulated by odor were analyzed based on the results of calcium imaging.

Specifically, before performing the calcium imaging assay, the coverslip substrate was combined with a magnetic chamber (Live Cell instrument, Seoul, Korea), and the medium was replaced with KREBS Ringer's buffer containing 115 mM NaCl, 5.9 mM KCl, 2.5 mM $CaCl_2 \cdot 2H_2O$, 1.2 mM $MgCl_2$, 1.2 mM $NaH_2PO_4$, 10 mM HEPES sodium salt, and 10 mM D-glucose, and it was washed with PBS. Then, the cells were stained with fluo3-AM (life technologies, Waltham, USA). Fluorescence images of calcium markers were monitored using a confocal microscope. To stimulate the ORN, three odorants of 100 UM isovaleric acid (IVA), 2-isobutyl-3-methoxypyrazine (IBMP), and citralva, which are reported to activate the major signaling pathways of the ORN, and 100 UM of their mixture were applied to the magnetic chamber using a tubing connected to a syringe. The intracellular calcium concentration was calculated from the background corrected fluorescence ratio at 506/526 nm using a two-point calibration scheme and the equation $$[Ca]_i = K_d(F_0/F_s)(R-R_{min})/(R_{max}-R).$$

Figure 12:
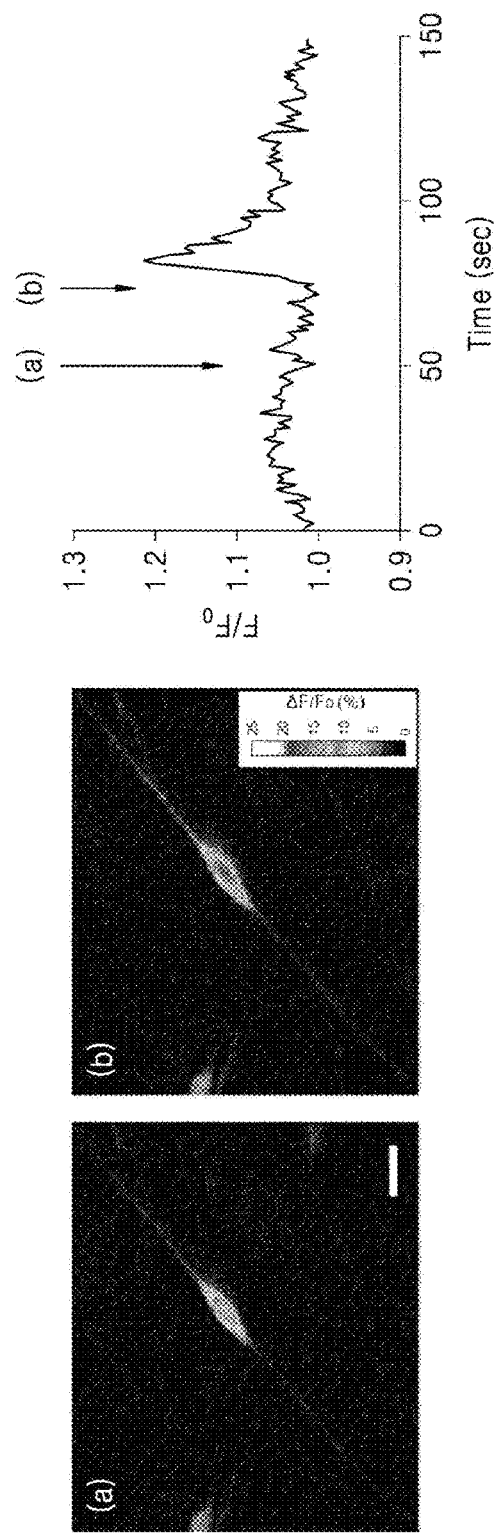
FIG. 12 shows fluorescence images of odor-activated ORNs (A), and increased fluorescence intensity of calcium markers upon stimulation of a deodorant mixture (B).

As a result, as shown in FIG. 12, it was determined that ORN differentiated from the spheroid cultured progenitor cells exhibits their activity normally by stimulation of the deodorant mixture.

Figure 13:
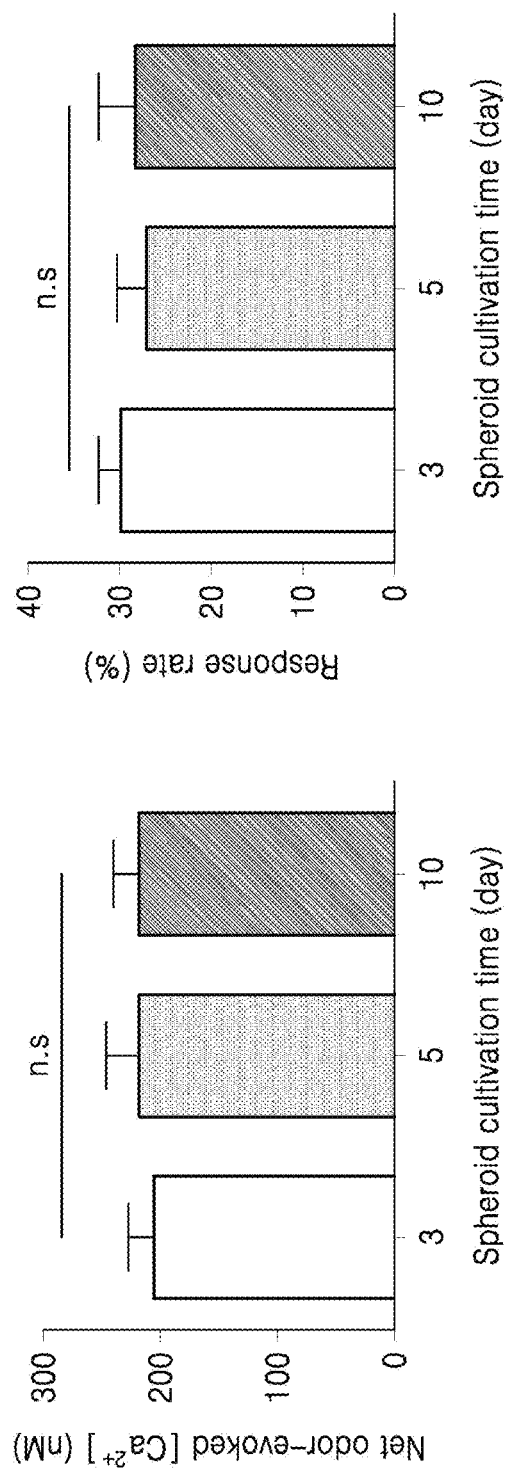
FIG. 13 is a diagram showing total intracellular calcium concentration evoked by odor of ORN progenitor cells (A) and a response rate (B) according to spheroid cultivation time.

In addition, as shown in FIG. 13A, the calculated averages of the total concentrations stimulated by odor in ORNs spheroid cultured for 3 days, 5 days and 10 days were 195.7±24.0 nM, 205.3±24.9 nM, and 205.4±22.3 nM, respectively. However, these values did not show statistically significant difference among the three different groups.

Response rates were calculated as a ratio of the number of activated cell populations to the total number of cell populations in the confocal microscopy software. As a result, as shown in FIG. 13B, the response rates calculated according to the cultivation time of 3 days, 5 days, and 10 days were 29.9±2.5%, 27.6±3.0%, and 28.1±4.2%, respectively. However, these values also did not show statistically significant difference among the three different groups.

Figure 14:
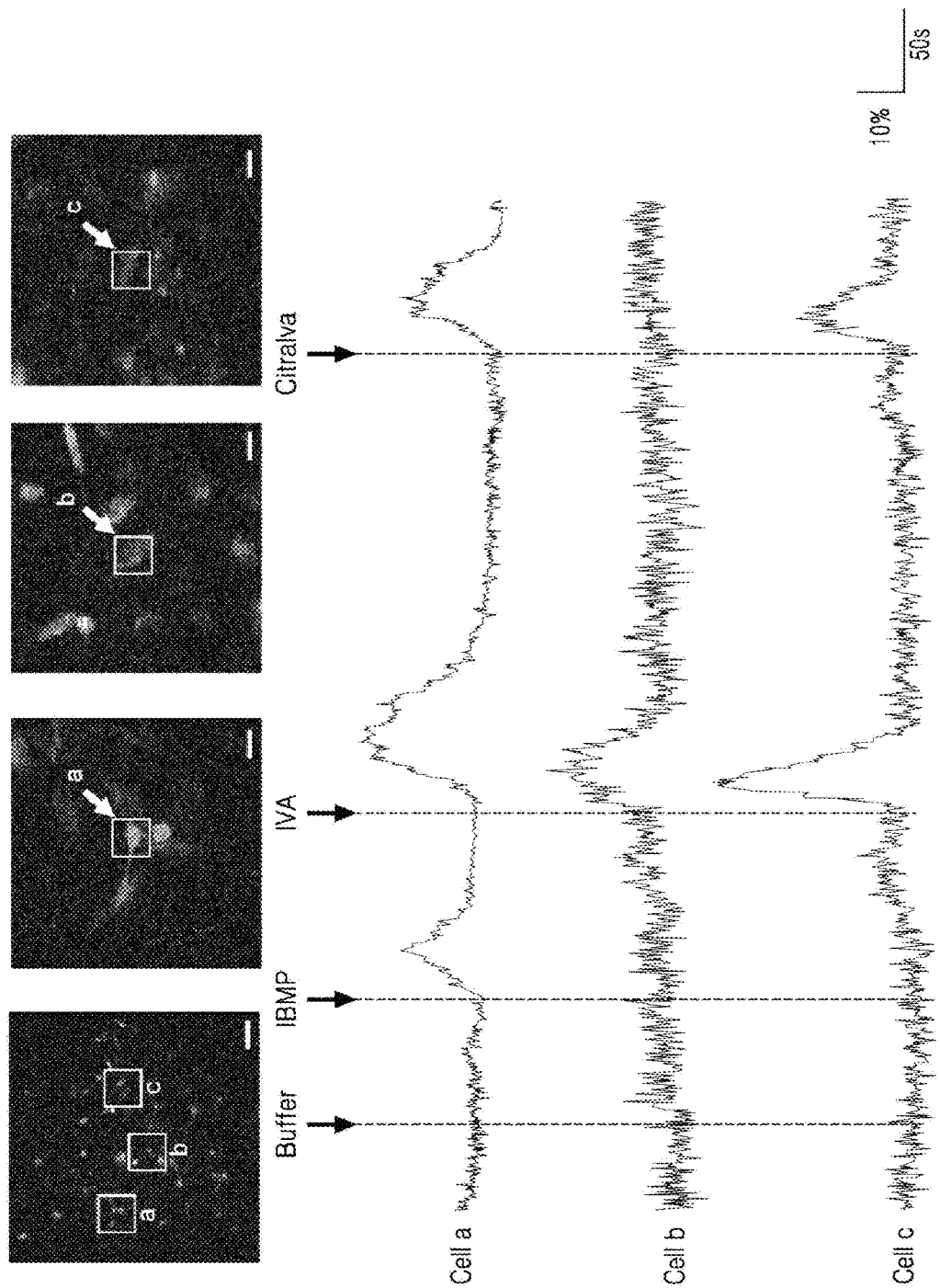
FIG. 14 shows changes in fluorescence intensity according to deodorant stimulation. The first image from the upper left is a confocal microscope image (scale bar=200 μm), and the second to fourth images from the left are enlarged images (scale bar=40 μm).

Next, to determine the physiological properties of ORNs under single deodorant stimulation, the changes in intracellular calcium levels of ORNs and the changes in fluorescence intensity in cells a, b and c according to deodorant stimulation were monitored using 100 μM IBMP, 100 μM IVA, and 100 μM citralva. As a result, as shown in FIG. 14, the cell a was activated in response to all deodorant stimuli, the cell b was activated by IVA, and the cell c was activated by IVA and citralva.

That is to say, the above results indicate that ORN differentiated from spheroid cultured progenitor cells has a reliable activation rate upon stimulation with deodorant.

5-2. Demonstration of the Effect of Extending the Storage Period by Cryopreservation Since the neural stem cells cultured into spheroids need to be stably preserved for a long period of time for efficient use, in order to determine whether or not the cell storage period is extended through cryopreservation, spheroid-cultured ORN progenitor cells were cryopreserved for 35 days and thawed to test their physiological properties.

Figure 15:
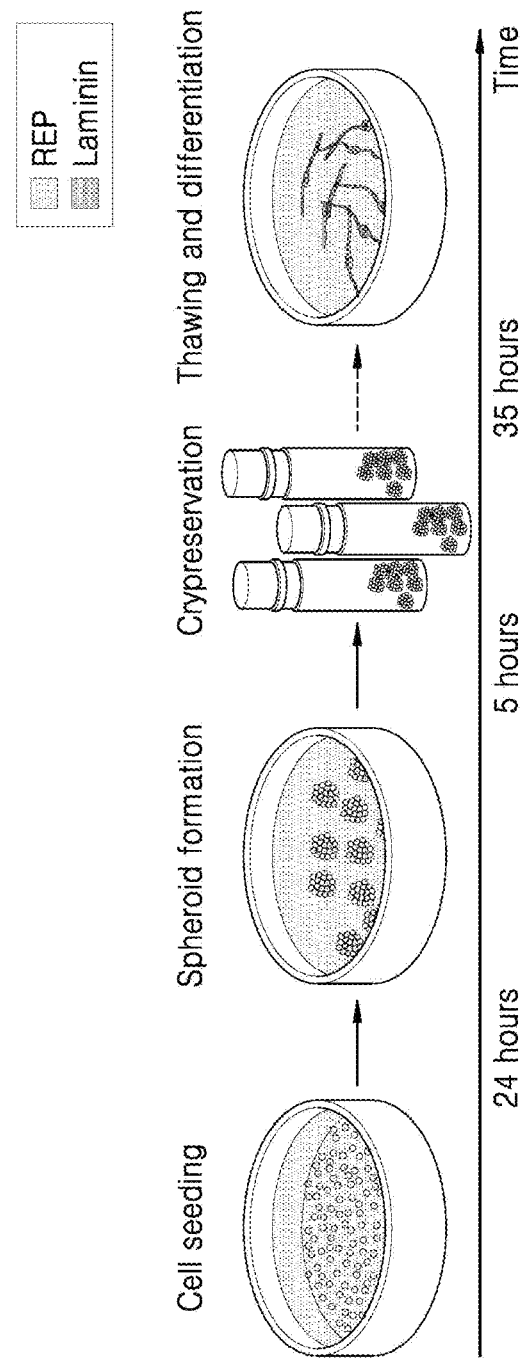
FIG. 15 is a diagram showing a process of cryopreservation, thawing and differentiation of ORN progenitor cells cultured into spheroids.

Specifically, as shown in FIG. 15, the 5 day spheroid ORN progenitor cells were cryopreserved using 10% DMSO and 20% FBS solution, and after 35 days, the cells were thawed on a plate coated with laminin to induce differentiation.

Figure 16:
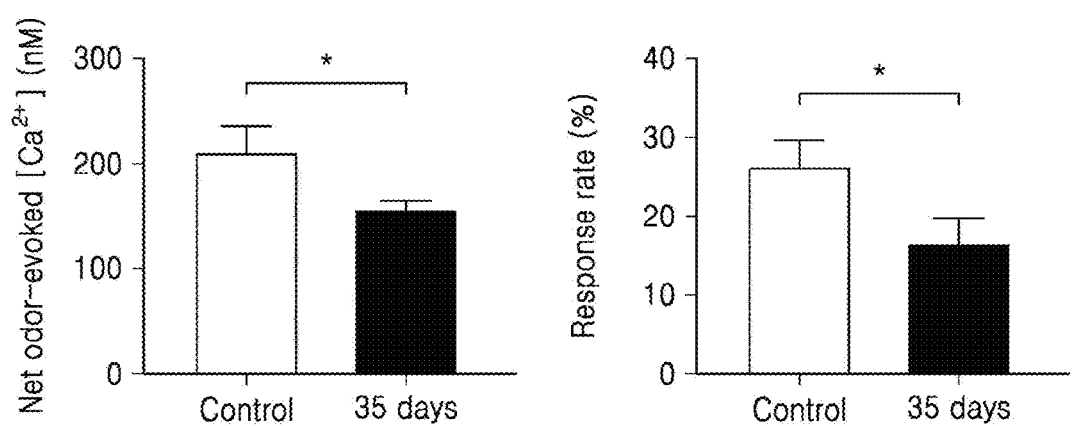
FIG. 16 shows diagrams illustrating total intracellular calcium concentration evoked by odor of ORNs differentiated from cryopreserved ORN progenitor cells (A) and response rate (B). (Number of experiments=8, total number of monitored cells=75, *<0.05)

As a result, as shown in FIG. 16, the total-calcium concentration and response rate stimulated by the odor of ORN differentiated from spheroid progenitor cells on day 35 were slightly decreased to 72.5% and 72.3%, respectively, compared to the physiological characteristics of ORN differentiated from spheroid progenitors on day 5, but the storage period was extended to 30 days. That is to say, it can be seen that the spheroid cultured ORN progenitor cells have the effect of extending the storage period through cryopreservation.

The present invention has been described with reference to preferred embodiments. Those skilled in the art to which the present invention pertains would understand that the present invention can be implemented in a modified form without departing from the principles and spirit of the present invention. Therefore, the disclosed embodiments are to be considered as illustrative rather than restrictive. The scope of the present invention is defined by the appended claims, not by the foregoing descriptions, and all differences within the equivalent scope thereto should be construed as being included in the present invention.

What is claimed is:

1. A method of culturing neural stem cells into spheroids, the method comprising:
   culturing neural stem cells in a culture vessel coated with a protein including a VGVPG pentapeptide and an RGD integrin receptor ligand; and
   isolating the neural stem cells that are aggregated and formed into spheroids during the culturing,
   wherein the neural stem cells are olfactory nerve receptor progenitor cells.

2. The method according to claim 1, wherein the protein is composed of the amino acid sequence of SEQ ID NO: 22.

3. The method according to claim 1, wherein the protein is coated at a concentration of 1 to 10 μM.

4. The method according to claim 1, wherein the neural stem cells are aggregated to form spheroids within 1 hour to 24 hours of the culturing.

5. The method according to claim 1, wherein the diameter of the spheroids of the neural stem cells is 50 to 80 μm.

6. The method according to claim 1, wherein the culturing is sub-culturing.

7. The method according to claim 6, wherein stemness of the neural stem cells is maintained during the sub-culture.

8. The method according to claim 1, further comprising primary culturing the neural stem cells.

9. The method according to claim 1, wherein the culturing is performed at a temperature of 35° C. to 40° C.

10. The method according to claim 1, wherein during the culturing, the neural stem cells are seeded at a cell concentration of $1\times10^5$ to $1\times10^7$ cells/ml.

* * * * *